US010751763B2

(12) United States Patent
Marencik et al.

(10) Patent No.: US 10,751,763 B2
(45) Date of Patent: Aug. 25, 2020

(54) GAS SAMPLING METHODS

(71) Applicant: Airgas, Inc., Radnor, PA (US)

(72) Inventors: Frederick Marencik, Lawrenceville, NJ (US); Robert J. Grasmeder, Perkasie, PA (US)

(73) Assignee: Airgas, Inc., Radnor, PA (US)

( * ) Notice: Subject to any disclaimer, the term of this patent is extended or adjusted under 35 U.S.C. 154(b) by 403 days.

(21) Appl. No.: 15/609,319

(22) Filed: May 31, 2017

(65) Prior Publication Data

US 2018/0348095 A1  Dec. 6, 2018

(51) Int. Cl.
| | | |
|---|---|---|
| *F17C 13/04* | (2006.01) | |
| *B08B 5/00* | (2006.01) | |
| *G01N 33/00* | (2006.01) | |
| *G01F 1/26* | (2006.01) | |
| *B08B 9/032* | (2006.01) | |
| *G01N 1/00* | (2006.01) | |

(52) U.S. Cl.
CPC .............. *B08B 5/00* (2013.01); *B08B 9/0328* (2013.01); *F17C 13/04* (2013.01); *G01F 1/26* (2013.01); *G01N 33/0029* (2013.01); *F17C 2227/044* (2013.01); *F17C 2260/056* (2013.01); *G01N 2001/002* (2013.01)

(58) Field of Classification Search
CPC ......... F17C 13/04; B08B 5/00; B08B 9/0328; G01N 2001/002
See application file for complete search history.

(56) References Cited

U.S. PATENT DOCUMENTS

| | | | | |
|---|---|---|---|---|
| 5,240,024 | A * | 8/1993 | Moore | F17C 13/04 |
| | | | | 137/38 |
| 6,343,627 | B1* | 2/2002 | Hasaka | F17C 5/06 |
| | | | | 141/18 |
| 2003/0226588 | A1* | 12/2003 | Olander | F17C 5/00 |
| | | | | 137/240 |

OTHER PUBLICATIONS

Air Liquide, Achieve Optimal analytical accuracy, 2015, pp. 1-2 (Year: 2015).*

* cited by examiner

*Primary Examiner* — Lisa M Caputo
*Assistant Examiner* — Alex T Devito
(74) *Attorney, Agent, or Firm* — Elwood L. Haynes (57) ABSTRACT

A method for utilizing a gas sampling panel is provide, including at least one system sample gas inlet, a purge gas inlet, a system outlet, a system vent outlet, a purge gas valve, at least one manifold station valve, a regulator isolation valve, a regulator, a flow meter inlet valve, a flow meter, a flow meter outlet valve, a relief valve, a process valve, a process check valve, a purge check valve, and a vent check valve.

12 Claims, 12 Drawing Sheets

First Conduit

Figure 2b
First Conduit

Figure 2c
Second Conduit

Figure 2d
Third Conduit

Figure 3 - (First Circuit)
Direct Flow Circuit

Figure 4 - (Second Circuit)
Flow Control Circuit

Figure 5 – (Third Circuit)
Sample with Bypass Circuit

Figure 6a – (Fourth Circuit)
Panel Purge Circuit
(with Adapter Valve)

Figure 6b – (Fourth Circuit)
Panel Purge Circuit
(Connected to Sample Cylinder)

Figure 7 – (Fifth Circuit) Sample Purge Circuit

GAS SAMPLING METHODS

BACKGROUND

Purging is an important procedure which is often overlooked in many gas processes. A method of purging, known as pressure cycle purging, is used on complex systems with dead end passages where a steady flow of inert gas cannot flush all areas of the system. Pressure cycle purging is normally accomplished using an inert purge gas such as clean extra dry nitrogen. Before initial and subsequent system startups, purging should be done to remove contaminants (such as air and water vapor) from the gas delivery system. To enhance operator safety, purging should also be performed before changing out cylinders to protect operators from exposure of corrosive or toxic gases.

Oxygen and moisture can adversely affect many applications, potentially reducing the quality of products being produced, or affecting the results of tests being performed. After cylinder connection, contamination from atmospheric air and water vapor (moisture) may adversely affect many applications (inaccurate processes, reduce HCL response, etc.); reduce the quality of the calibration gas (inaccurate control measurements, slow cycle—calibration times); affect the results of tests being performed; react with gases to form highly corrosive acids that react with most metals including stainless steel, thereby reducing service life of gas handling and application equipment (safety, repair and maintenance issues may be encountered); and/or react with iron and HCL to form iron oxide (rust).

Superior equipment design with the use of robust materials of construction and purging techniques will help avoid and eliminate these and other related problems from occurring. There is a need in the industry for a sample system incorporating proper purging methods for the sampling of reactive gases used in highly sensitive calibration and analysis applications

SUMMARY OF THE INVENTION

In one embodiment of the present invention, a method for utilizing a gas sampling panel is provided, which includes at least one system sample gas inlet, a purge gas inlet, a system outlet, a system vent outlet, a purge gas valve, at least one manifold station valve, a regulator isolation valve, a regulator, a flow meter inlet valve, a flow meter, a flow meter outlet valve, a relief valve, a process valve, a process check valve, a purge check valve, and a vent check valve. The sample gas inlet is fluidically connected to the at least one manifold station valve, the purge gas inlet is fluidically connected to a purge check valve inlet port; a purge check valve outlet port is fluidically connected to a purge gas valve inlet port; a first conduit fluidically connects a purge gas valve outlet port, a manifold station valve outlet port, and a regulator isolation valve inlet port; a regulator isolation valve outlet port is fluidically connected to a regulator inlet port; the flow meter inlet valve is connected as follows: a second conduit fluidically connects a flow meter valve inlet port to a regulator outlet port, a first flow through gas inlet port, and a second flow through gas inlet port, the first flow through gas inlet port is fluidically connected to the process valve first inlet port, the second flow through gas inlet port is fluidically connected to a relief valve inlet port, and a flow meter inlet valve controlled gas outlet port is fluidically connected to a flow meter inlet port; a flow meter outlet port is fluidically connected to a flow meter outlet valve inlet port, a flow meter outlet valve first outlet port is fluidically connected to a process valve second inlet port; a process valve outlet port is fluidically connected to a process check valve inlet port, a process check valve outlet port is fluidically connected to the system outlet, a third conduit fluidically connects a relief valve outlet port, a flow meter outlet valve second port, and a vent check valve inlet port; a vent check valve outlet port is fluidically connected to the system vent outlet. The method includes introducing gas into the sample gas inlet and/or the purge gas inlet, and removing gas from the system outlet and/or the system vent outlet.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

ELEMENT NUMBERS

101=purge gas inlet
102=purge check valve

103=purge gas valve
105=manifold station valve
106=regulator isolation valve
107=pressure regulator
108=relief valve
109=flow meter inlet valve
110=flow meter
111=process valve
112=process check valve
113=system outlet
114=flow meter outlet valve
116=vent check valve
117=system vent outlet
118=adaptor valve
119=flow meter metering valve
120=pigtails
121=CGA connection nut
122=sample gas source
123=purge gas cylinder valve
124=purge gas source
125=first conduit
126=second conduit
127=third conduit
128=first flow through gas port
129=second flow through gas port
130=sample gas cylinder valve
132=purge gas pressure regulator
133=sample gas inlet manifold

DESCRIPTION OF PREFERRED EMBODIMENTS

A regulator control panel is proposed that is designed to deliver reactive gas mixtures (preferably HCl calibration standards) of a fixed concentration from a gas cylinder to a gas analyzer with negligible loss of HCl in transit. This proposed gas delivery system, with the proposed purging and sampling methods, provides for a safe and accurate delivery of calibration standards with CEMS commissioning, QC and QA applications. The proposed regulator control panel minimizes (or eliminates) HCL loss during the transfer of gas from the cylinder to the analyzer. The proposed regulator control panel also achieves a stable response for HCl from an analyzer in a short period of time, thus saving time by accelerating the analysis. The proposed regulator control panel also minimizes (or eliminates) corrosion of analytical systems by HCl. And the proposed regulator control panel conserves HCl calibration gas, thereby also saving money.

The panel design utilizes wetted areas, including components with very small dead spaces, which have an inert coating. As used herein, the term "dead space" is defined as a portion of a circuit wherein the fluid may become stagnant during normal operation. The coating is inert (nonreactive) to highly active chemical compounds while preventing contamination, catalysis, and out-gassing with the sampling gas. A preferred coating is a flexible inert silicon-based coating (such as Silconert® 2000). The total volume of dead space is less than 5% of the total system volume, preferably less than 1% of the total system volume.

As used herein, the term "wetted material surfaces" are the surfaces of system components that come into direct contact with the process gas which include at least a manifold, manifold station valve, a purge gas valve, a regulator isolation valve, a pressure regulator, a flow meter inlet valve, a flow meter outlet valve, a process valve, a process check valve, and all interconnecting tubing.

The panel comprises adjustable two-stage pressure control valves and two switching valves allowing flow to either go through a flow meter (regulating flow to an instrument or vent) or directly to the instrument. These features allow the panel to utilize a sample by-pass loop. The sample by-pass loop allows the system to achieve a stable response from the analyzer in a shorter amount of time, thus saving time and accelerating the analysis of HCL.

As used herein, the term "sample by-pass loop" is defined as including at least a flow meter inlet valve, a flow meter with an integrated metering valve, a flow meter outlet valve, and a system vent outlet.

The panel design also includes a high pressure manifold featuring ¼-turn diaphragm-seal station, purge and regulator isolation valves ensuring high purity contaminant-free operation. During initial system start-up or when changing gas cylinders, the panel provides a safe and convenient means of pressure cycle purging the distribution system with a ultra dry nitrogen purge gas. The design includes lever-activated valves that operate from "fully closed" to "fully open" in a ¼-turn and 3-way switching valves with labeling allowing for quick activation and provide positive visual ID of open/closed or directional status. Color-coded ¼-turn handles may be included to serve as a visual aid in process control. Check valves are installed in the purge gas inlet, vent line and process outlet ports to prevent back flow of the gases into the respective lines. The system may be configured to accommodate more than one cylinder attached simultaneously.

Figure 3:
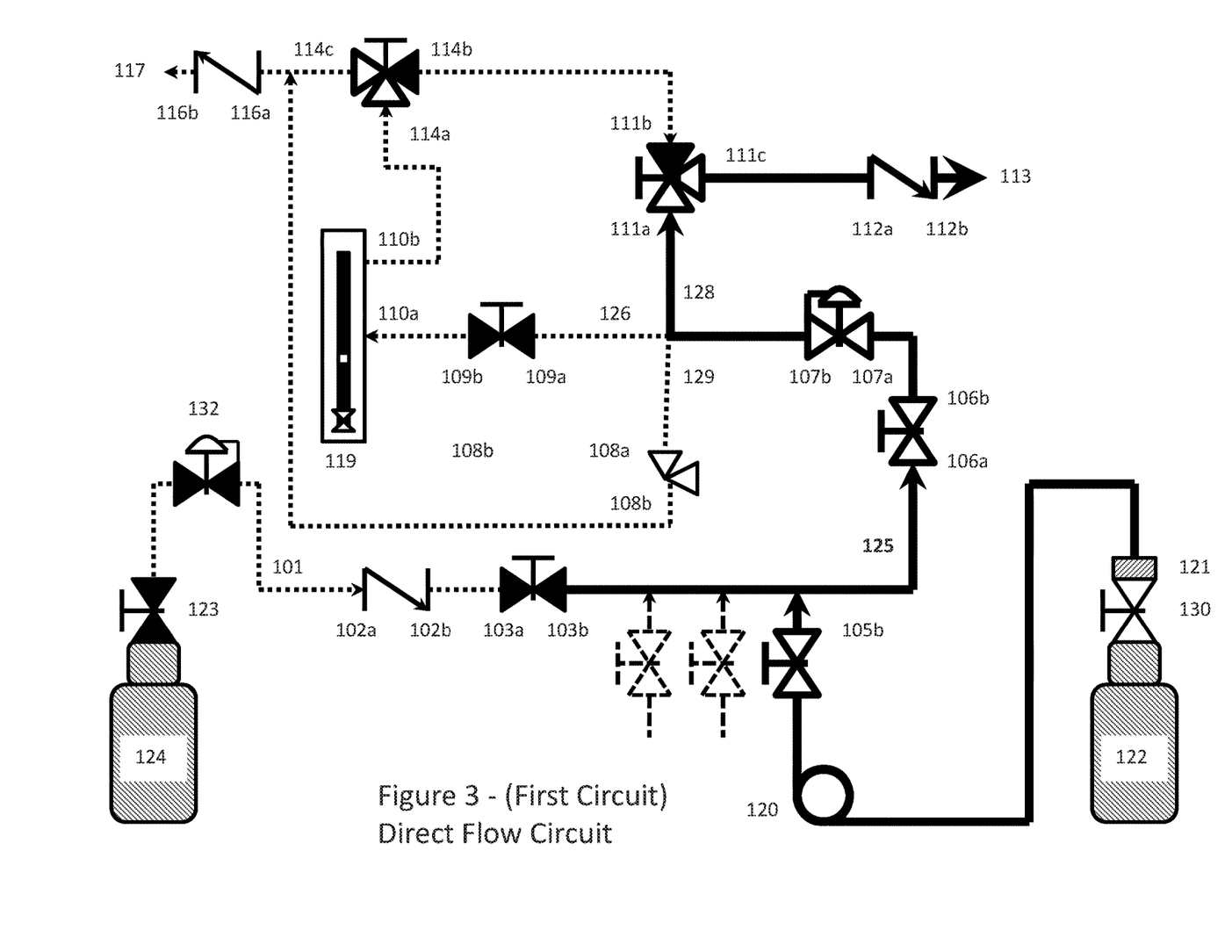
FIG. 3 is a schematic representation of the direct flow circuit ("first circuit") pathway through the regulator control panel, in accordance with one embodiment of the present invention.

As used herein, and as illustrated in FIG. 3, the term "direct flow circuit" ("first circuit") is defined as including at least a purge gas valve, at least one manifold station valve, a regulator isolation valve, a pressure regulator, a process valve, and a process check valve.

Figure 4:
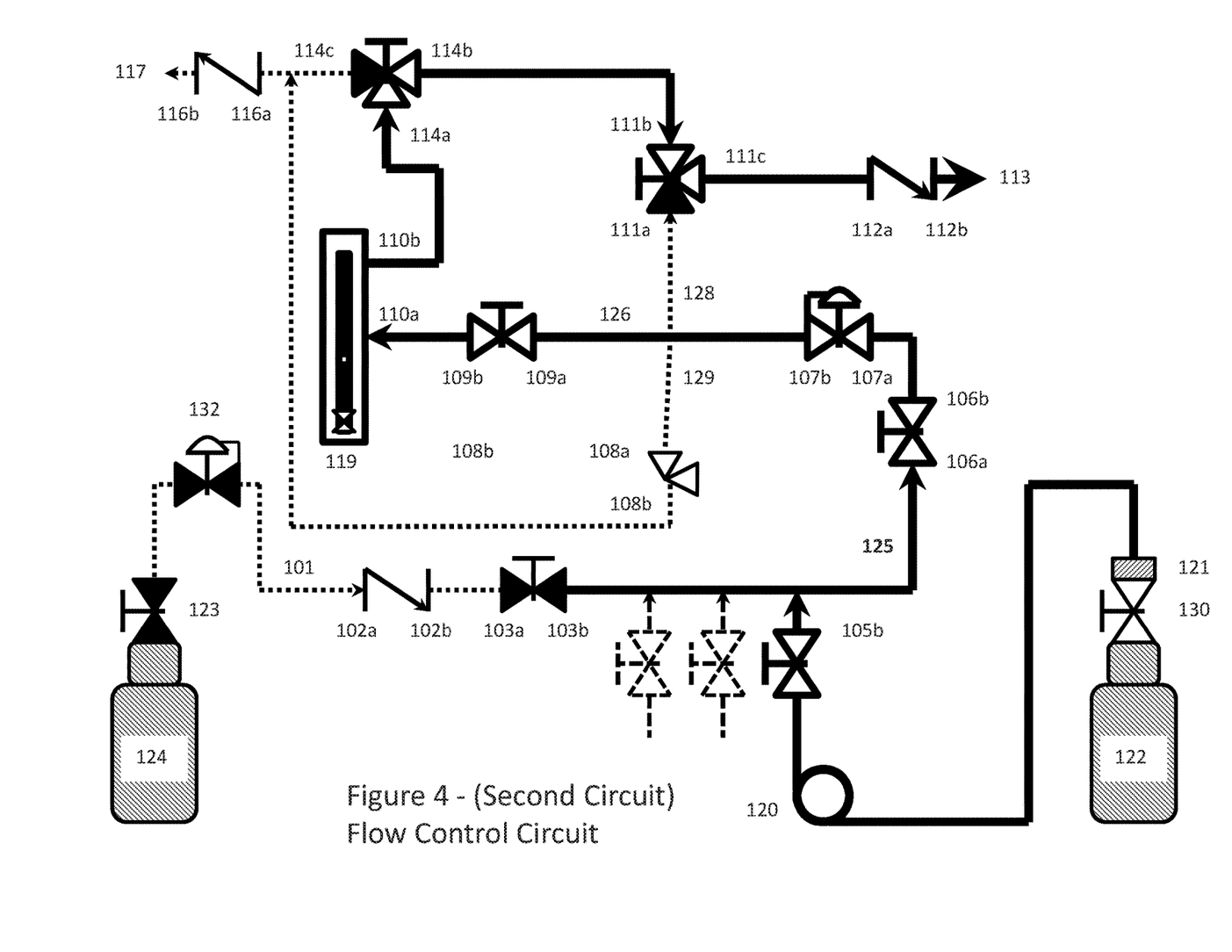
FIG. 4 is a schematic representation of the flow control circuit ("second circuit") pathway through the regulator control panel, in accordance with one embodiment of the present invention.

As used herein, and as illustrated in FIG. 4, the term "flow control circuit" ("second circuit") is defined as including at least a purge gas valve, at least a one manifold station valve, regulator isolation valve, a pressure regulator, a flow meter inlet valve, a flow meter with an integral metering valve, a flow meter outlet valve, a process valve, and a process check valve.

Figure 5:
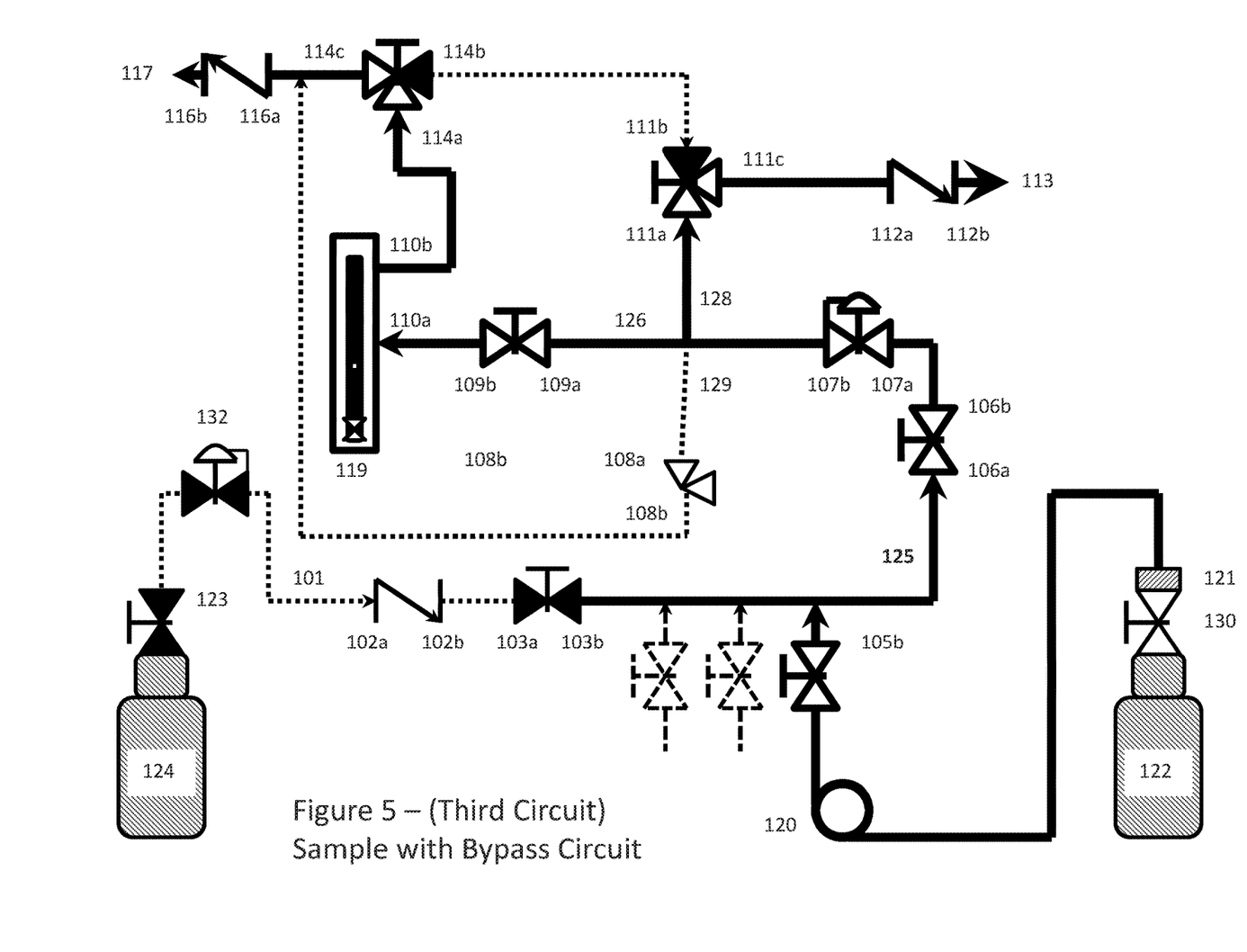
FIG. 5 is a schematic representation of the sample with bypass circuit ("third circuit") pathway through the regulator control panel, in accordance with one embodiment of the present invention.

As used herein, and as illustrated in FIG. 5, the term "sample with bypass circuit" ("third circuit") is defined as including at least a purge gas valve, at least one manifold station valve, a regulator isolation valve, a pressure regulator, a flow meter inlet valve, a flow meter with an integral metering valve, a flow meter outlet valve, a vent check valve, a process valve, and a process check valve.

Figure 6A:
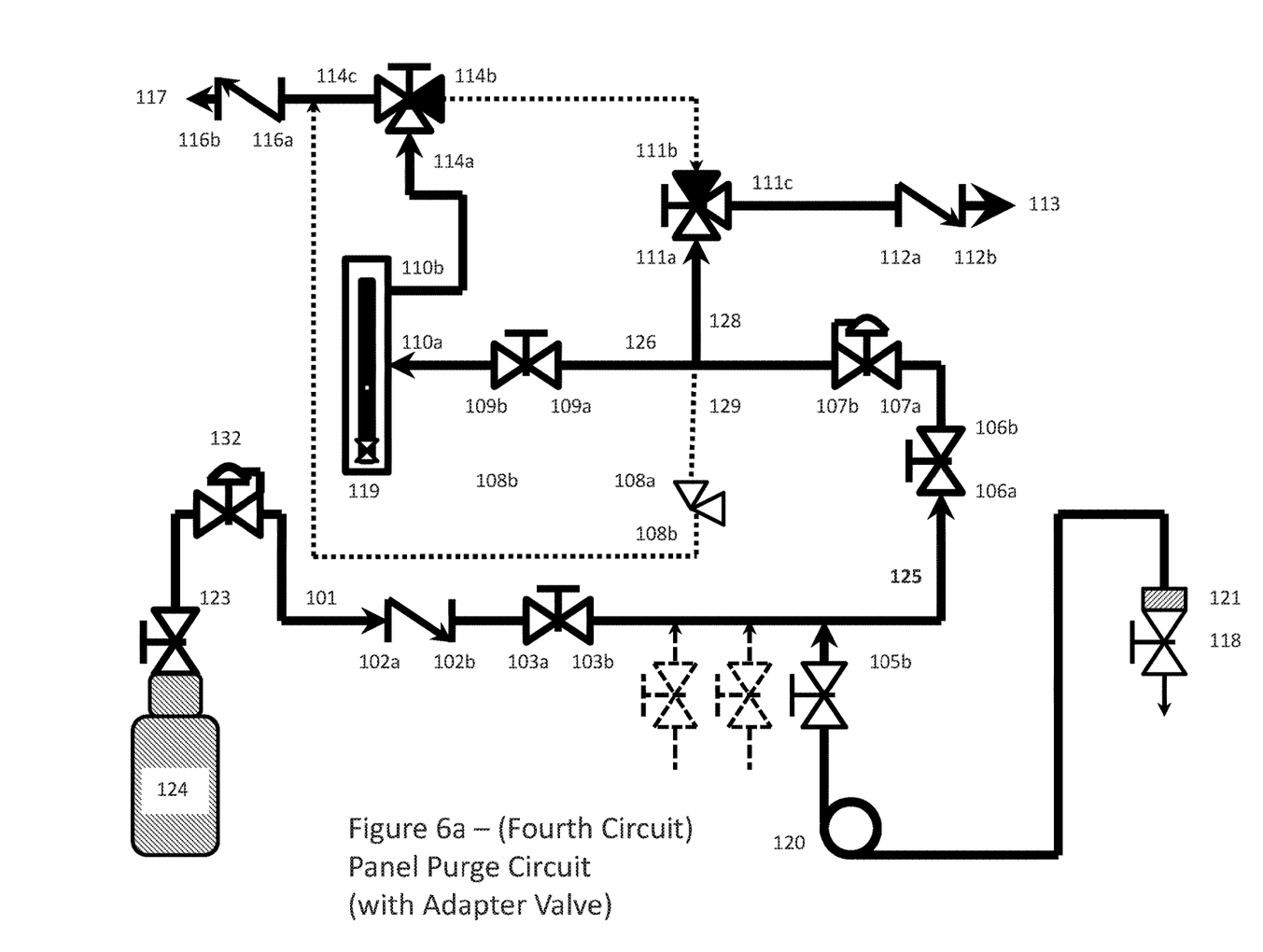
FIG. 6*a* is a schematic representation of the panel purge circuit ("fourth circuit") pathway through the regulator control panel, in accordance with one embodiment of the present invention.
Figure 6B:
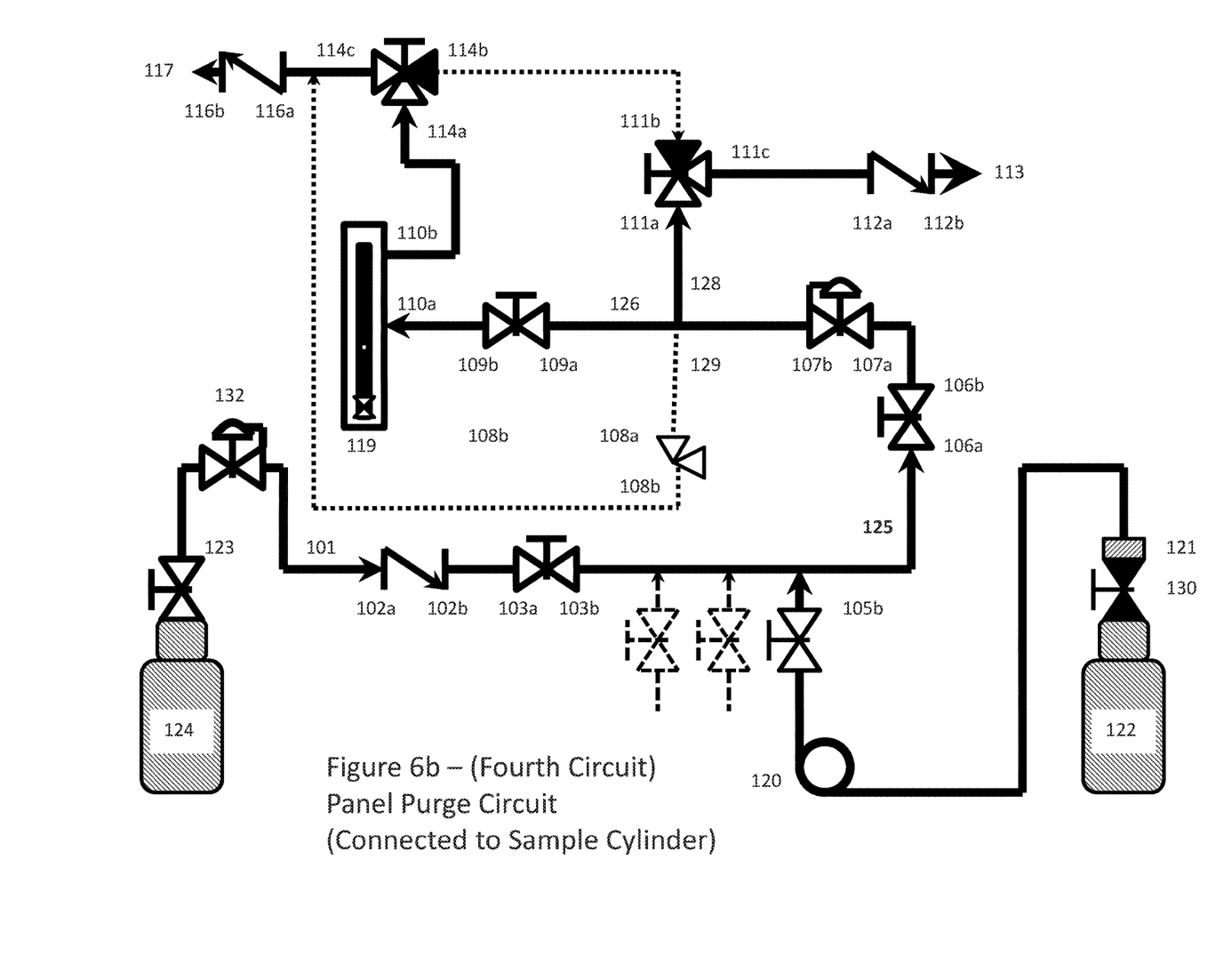
FIG. 6*b* is a schematic representation of the panel purge circuit ("fourth circuit") pathway through the regulator control panel, in accordance with one embodiment of the present invention.

As used herein, and as illustrated in FIGS. 6a and 6b, the term "panel purge circuit" ("fourth circuit") is defined as including at least a purge gas cylinder valve, a purge gas pressure regulator, a purge check valve, a purge gas valve, at least one manifold station valve, regulator isolation valve, a pressure regulator, a flow meter inlet valve, a flow meter with an integral metering valve, a flow meter outlet valve, a vent check valve and, a process valve, and a process check valve.

Figure 7:
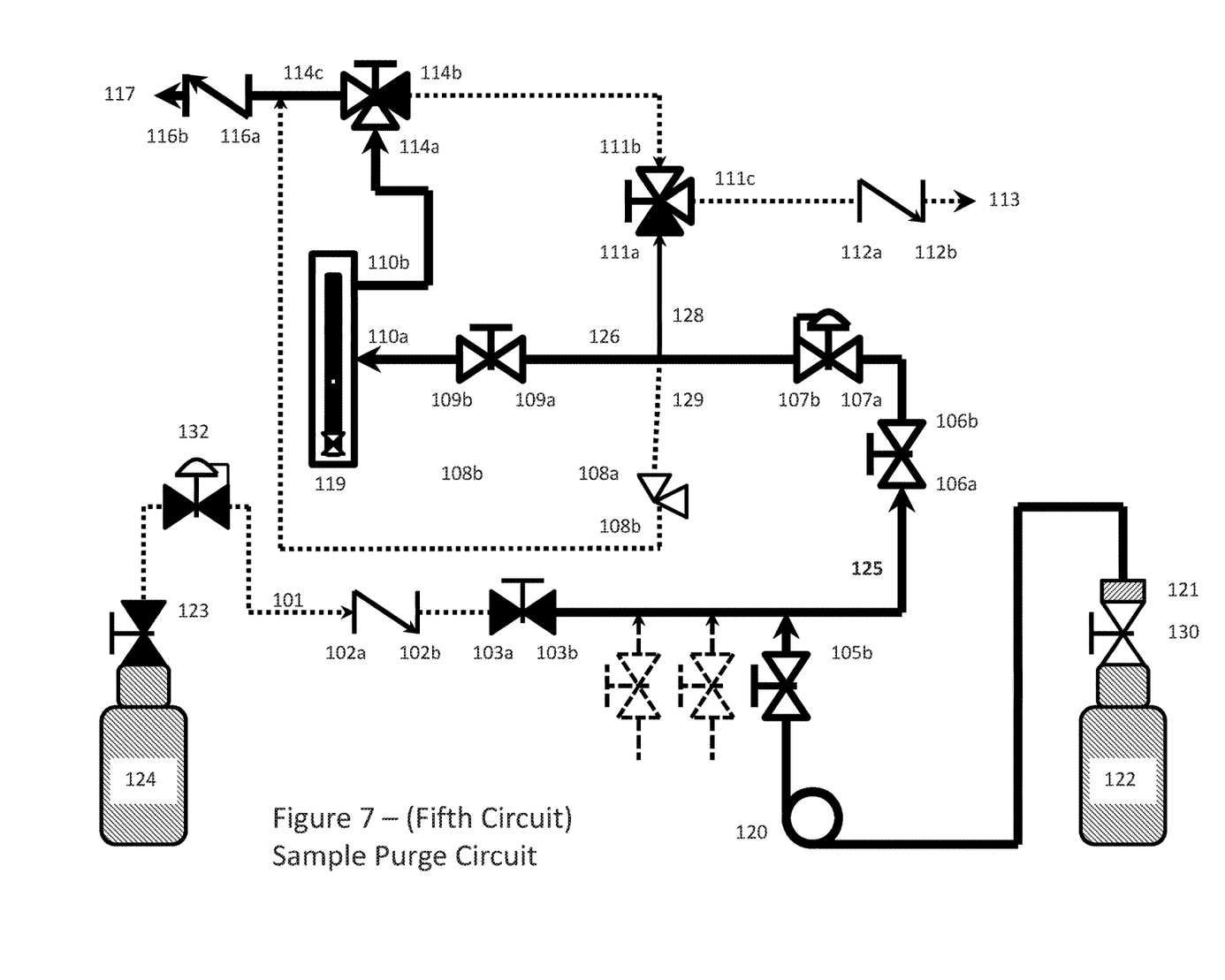
FIG. 7 is a schematic representation of the sample purge circuit ("fifth circuit") pathway through the regulator control panel, in accordance with one embodiment of the present invention.

As used herein, and as illustrated in FIG. 7, the term "sample purge circuit" ("fifth circuit") is defined as including at least a purge gas valve, at least one manifold station valve, regulator isolation valve, a pressure regulator, a flow meter inlet valve, a flow meter with an integral metering valve, a flow meter outlet valve, and a vent check valve.

Turning now to the Figures, a gas sampling panel will be described. The gas sampling panel (regulator control panel) includes a purge gas inlet 101, a system outlet 113, a system vent outlet 117, a purge gas valve 103, at least one manifold station valve 105, a regulator isolation valve 106, a pressure regulator 107, a flow meter inlet valve 109, a flow meter 110, a flow meter outlet valve 114, a relief valve 108, a process valve 111, a process check valve 112, a purge check valve 102, a CGA connection nut 121, and a vent check valve 116. The purge gas inlet 101 is fluidically connected to a purge check valve inlet port 102*a*. A purge check valve outlet port 102*b* is fluidically connected to a purge gas valve inlet port 103*a*.

Figure 2A:
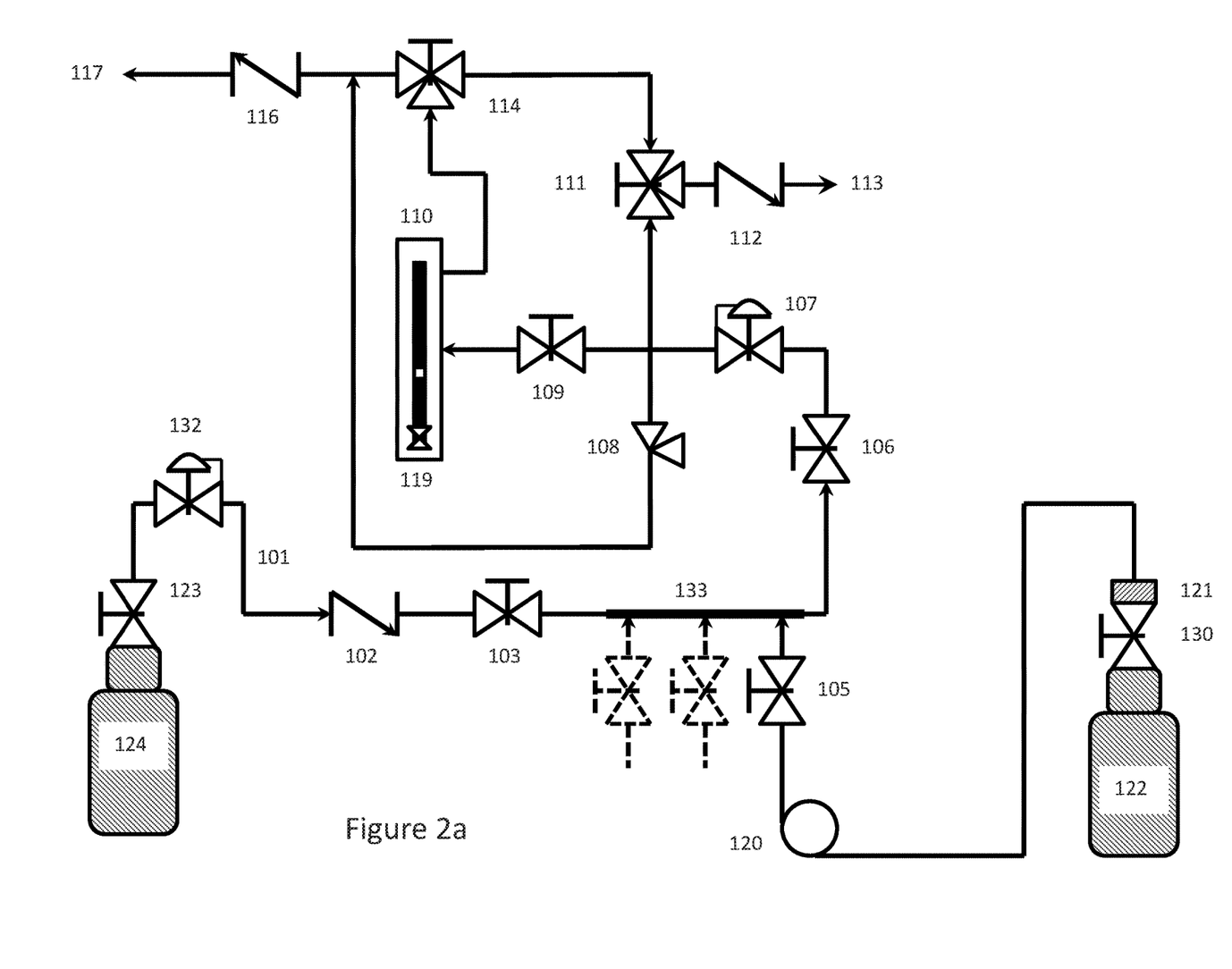
FIG. 2*a* is a schematic representation of the regulator control panel and the purge gas source, in accordance with one embodiment of the present invention.
Figure 2B:
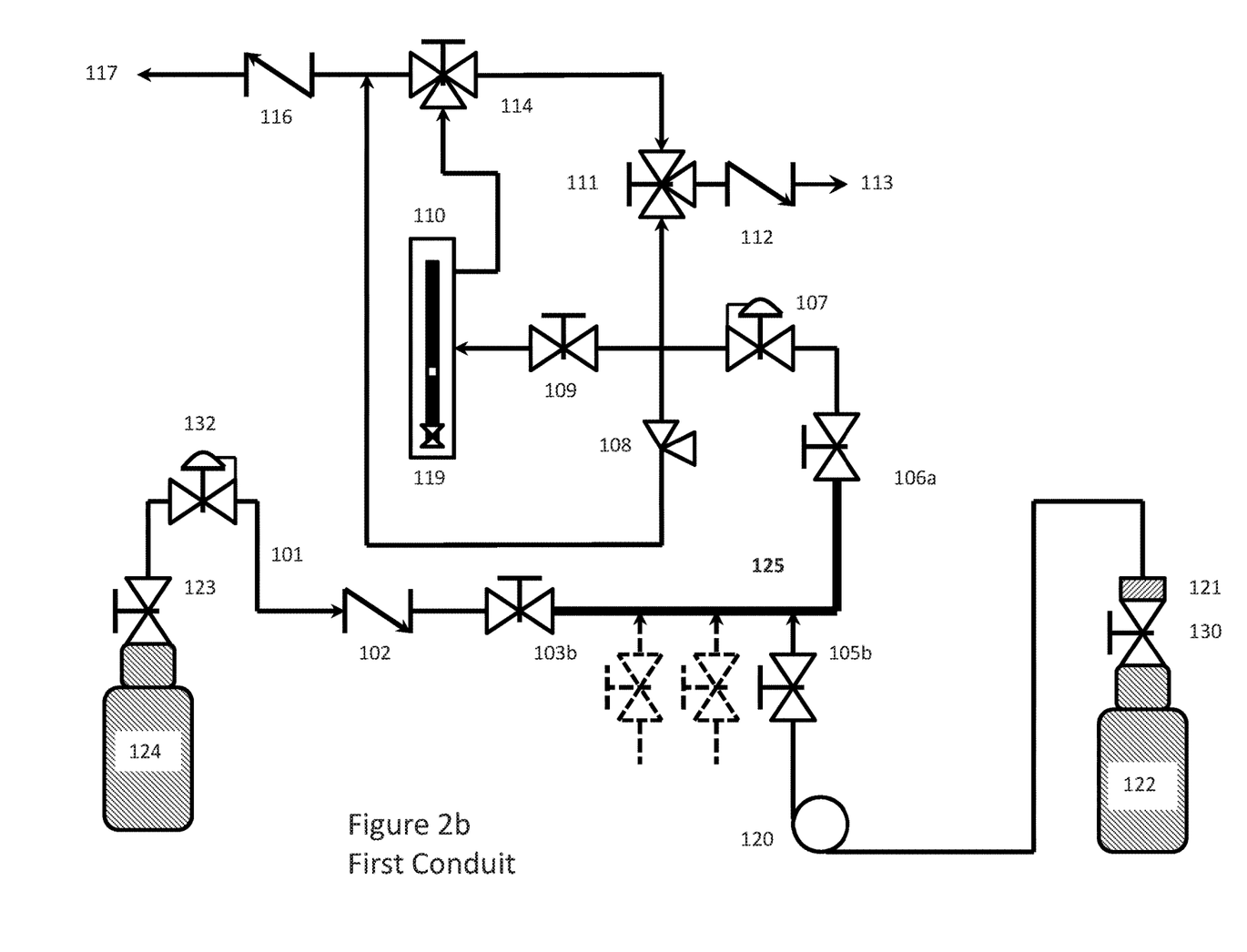
FIG. 2*b* is a schematic representation of the regulator control panel and the purge gas source, indicating the first conduit, in accordance with one embodiment of the present invention.

As illustrated in FIG. 2*b*, a first conduit 125 fluidically connects a purge gas valve outlet port 103*b*, a manifold station valve inlet port 105*b*, and a regulator isolation valve inlet port 106*a*.

Figure 1A:
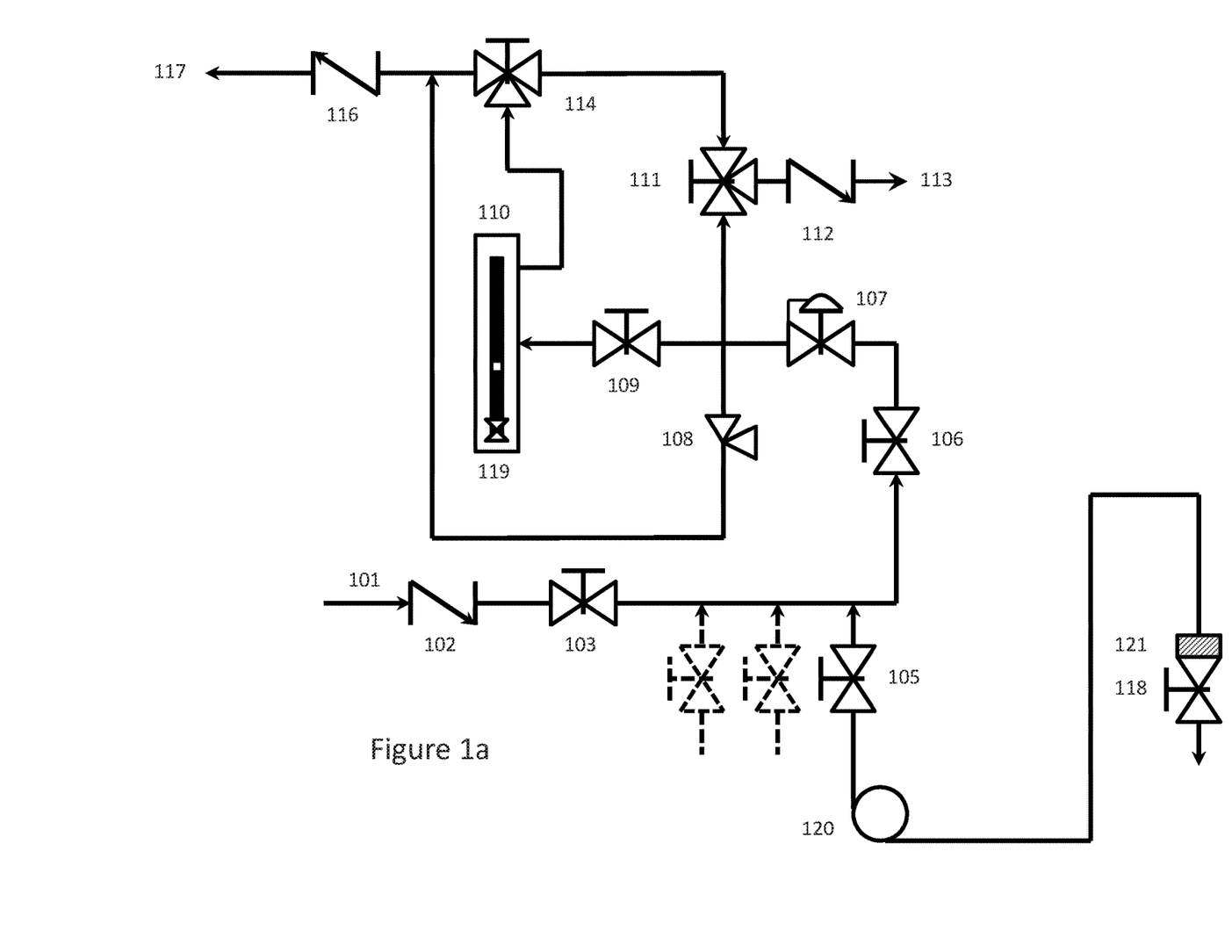
FIG. 1*a* is a schematic representation of the regulator control panel, in accordance with one embodiment of the present invention.
Figure 1B:
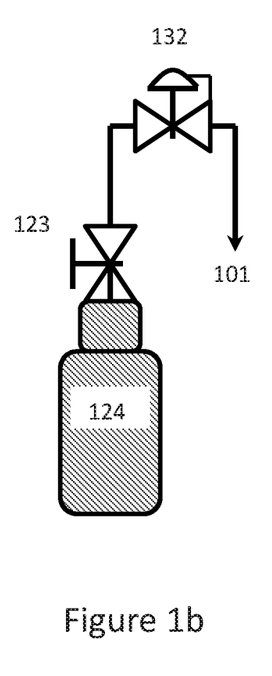
FIG. 1*b* is a schematic representation of the purge gas source, the purge gas cylinder valve, and the purge gas pressure regulator, in accordance with one embodiment of the present invention.

As indicated in FIGS. 1*a* and 6*a*, during the panel purging phase, adaptor valve 118, typically with a male CGA adapter, is connected to pigtail 120 by means of a CGA connection nut 121. In one embodiment, CGA connection nut 121 is a CGA 330. During the purging process, the adaptor valve 118 will be removed, and the CGA connection nut 121 will be attached to sample gas cylinder valve 130. Pigtail 120 leads into the at least one manifold station valve 105.

Once the panel has been purged, as indicated in FIG. 6*a*, during the panel purging phase, pigtail 120 is connected to sample gas cylinder valve 130 by means of a CGA connection nut 121, as indicated in FIG. 6*b*. In one embodiment, CGA connection nut 121 is a CGA 330. Pigtail 120 leads into one manifold station valve 105.

As indicated in FIGS. 2*a*, 3, 4, and 5 during the calibration phase (either Direct Flow Circuit; Flow Control Circuit; or Sample with Bypass Circuit), a sample gas source 122 with a gas cylinder valve 130 is connected to pigtail 120 by means of a CGA connection nut 121. In one embodiment, CGA connection nut 121 is a CGA 330. Pigtail 120 leads into the at least one manifold station valve 105. If more than one sample gas source 122 is used, an additional station valve 105 is employed. They connect to the system by means of sample gas inlet manifold 133.

Figure 2C:
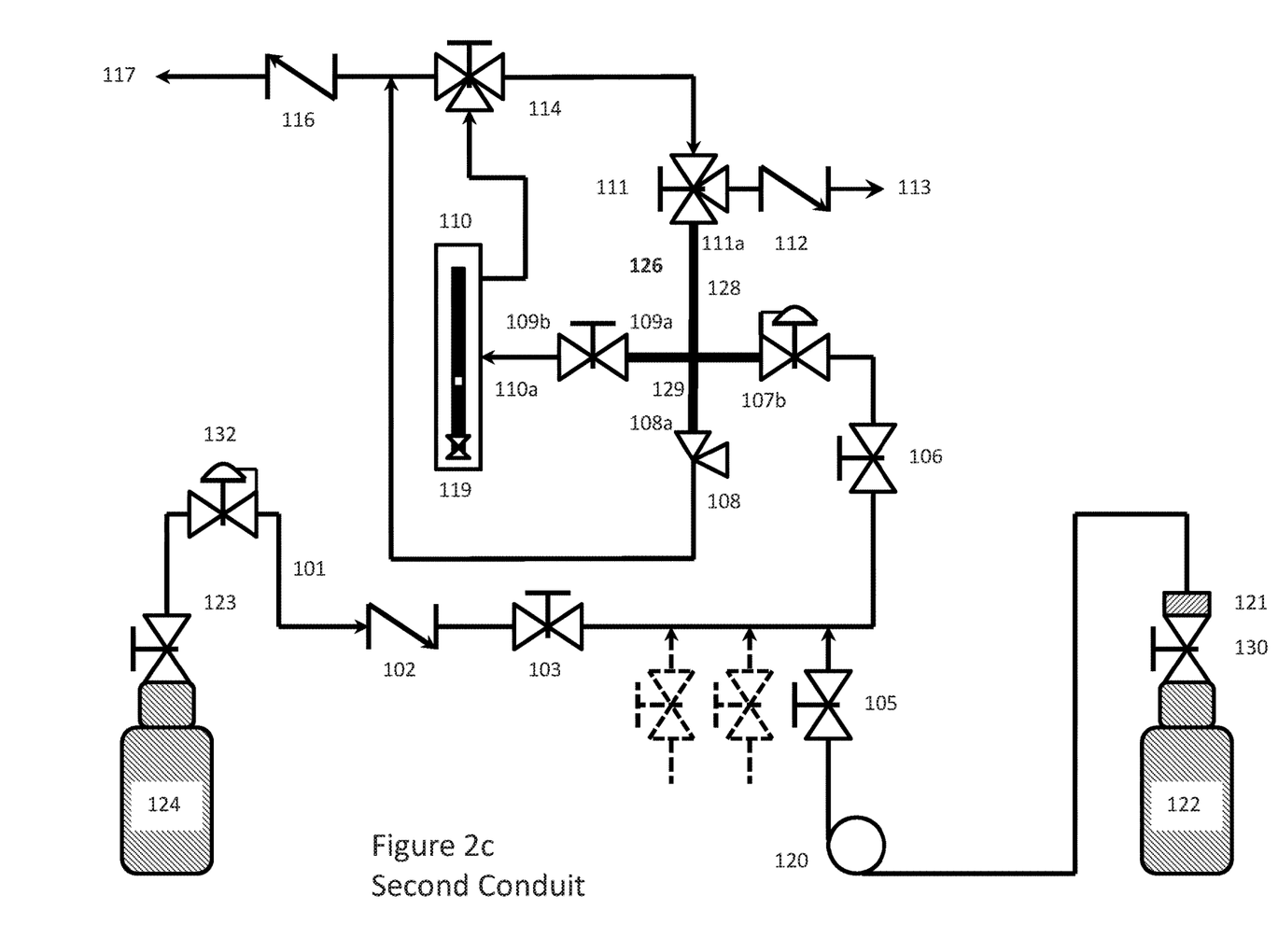
FIG. 2*c* is a schematic representation of the regulator control panel and the purge gas source, indicating the second conduit, in accordance with one embodiment of the present invention.

The flow meter inlet valve 109 is connected as follows. As illustrated in FIG. 2*c*, a second conduit 126 fluidically connects a flow meter inlet valve inlet port 109*a* to a pressure regulator outlet port 107*b*, a first flow through gas inlet port 128, and a second flow through gas inlet port 129. The first flow through gas inlet port 128 is fluidically connected to the process valve inlet port 111*a*. The second flow through gas inlet port 129 is fluidically connected to a relief valve inlet port 108*a*. And a flow meter inlet valve controlled gas outlet port 109*b* is fluidically connected to a flow meter inlet port 110*a*.

Returning to FIGS. 3, 4, and 5, a flow meter outlet port 110*b* is fluidically connected to a flow meter outlet valve inlet port 114*a*. A flow meter outlet valve first outlet port 114*b* is fluidically connected to a process valve second inlet port 111*b*. A process valve outlet port 111*c* is fluidically connected to a process check valve inlet port 112*a*. A process check valve outlet port 112*b* is fluidically connected to the system outlet 113.

Figure 2D:
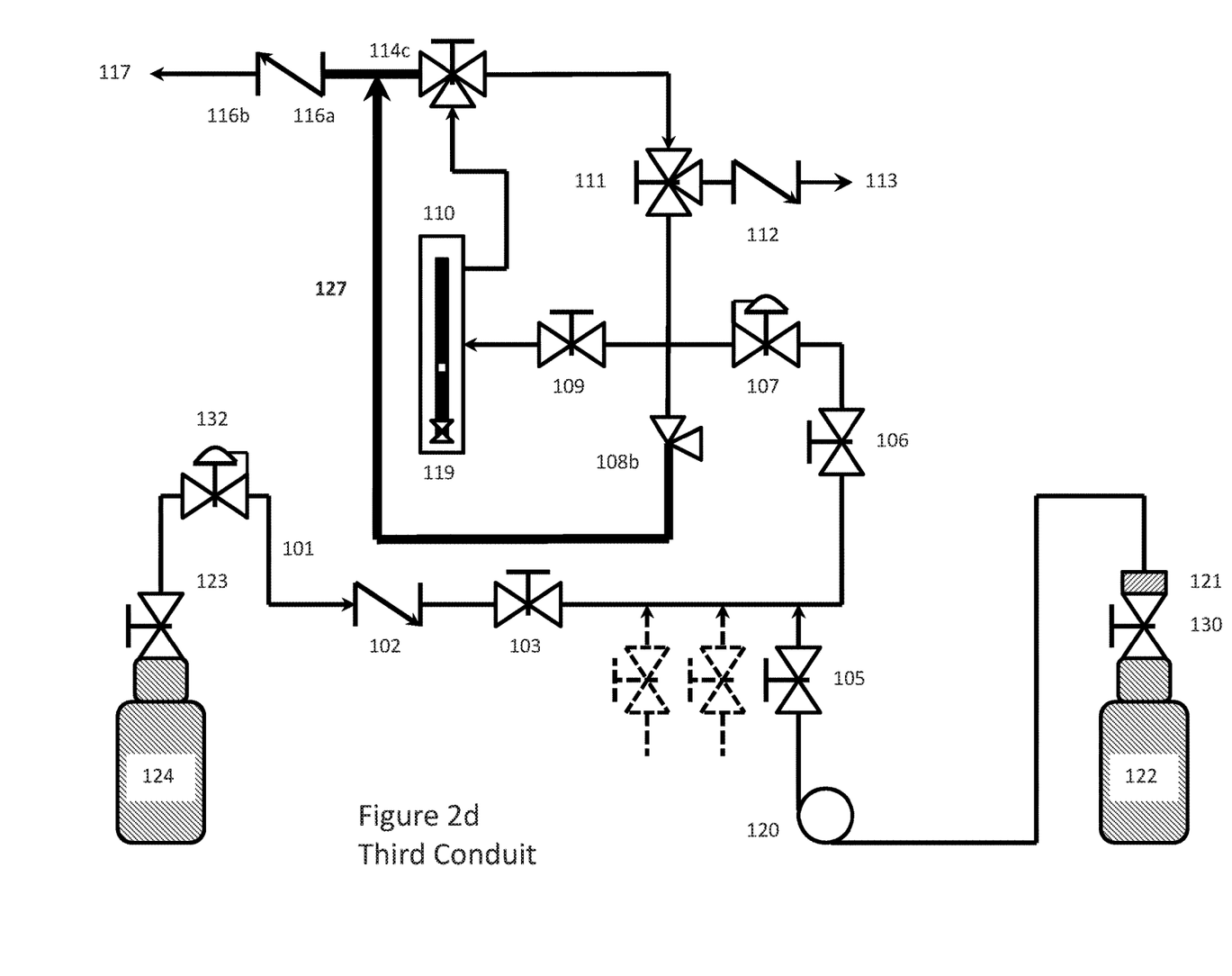
FIG. 2*d* is a schematic representation of the regulator control panel and the purge gas source, indicating the third conduit, in accordance with one embodiment of the present invention.

As illustrated in FIG. 2*d*, a third conduit 127 fluidically connects a relief valve outlet port 108*b*, a flow meter outlet valve second port 114*c*, and a vent check valve inlet port 116*a*. And a vent check valve outlet port 116*b* is fluidically connected to the system vent outlet 117.

The flow meter 110 may be a rotometer. The pressure regulator 107 may be adjustable to pressures between 0-75 psig. The flow meter inlet valve 109 may be configured to allow only flow through the outlet to be interrupted, and the flow through the first flow through gas inlet port 128 and the second flow through gas inlet port 129 cannot be interrupted.

The panel may include a flexible inert silicone coating on the wetted areas. The wetted areas are configured to provide a total volume of dead space that is less than 5% of the total system volume. The total volume of dead space may be less than 1% of the total system volume.

Purging

Panel Purge Circuit

With reference to FIGS. 6*a* and 6*b*, a panel purging process will be described. This step will remove entrapped air, moisture, or other gas contaminants in the entire system prior to calibration gas cylinder connection. The panel purge circuit, as previously defined, will be employed. At the start of this process all panel valves 103, 105, 106, 107, 109, 118, and 119 are closed. In addition valves 123, 130 and 132 are closed. The three-way process valve 111 is configured to receive a flow from pressure regulator 107; and the three-way flow meter outlet valve 114 is configured to direct a flow to vent check valve 116. Pressure regulator 107 is configured to deliver 0 psig (i.e. fully closed position).

A purge gas source 124 purge gas cylinder valve 123 must be connected to the purge gas pressure regulator 132. Typically, this will be nitrogen gas provided by a cylinder. The nitrogen purge gas must be extremely dry (H2O<100 ppb) for the delivery system to perform effectively as designed. The purge gas source 124 must be in line with a purge gas pressure regulator 132 with an adjustable pressure range of 0-75 psig. Purge gas cylinder valve 123 is opened to provide dry nitrogen to purge gas pressure regulator 132. The purge gas pressure regulator 132 is then opened and adjusted to the desired pressure. In a preferred embodiment, the pressure regulator 132 is set to 20 psig.

As illustrated in FIG. 6*a*, the purge gas valve 103 is now opened, to allow the flow of ultra dry nitrogen into the panel. The manifold station valve 105 is now opened. As the nitrogen flows through the manifold 133, the adaptor-valve 118 is slowly opened, to allow nitrogen to flow out of the pigtail 120 through the adapter-valve 118. As the nitrogen flows out of the opened adaptor-valve 118, the adapter valve 118 is carefully removed from CGA connection 121. The CGA connection 121 and pigtail 120 is then attached to the sample gas cylinder valve 130 as illustrated in FIG. 6*b*.

The regulator isolation valve 106 is then opened to allow purge nitrogen to flow into and pressurize the pressure regulator 107. The pressure regulator 107 is then adjusted to the desired pressure. In a preferred embodiment, the pressure regulator 107 is set to 20 psig. Purge gas flows through process valve 111, into process check valve 112 and out of the system. The flow meter inlet valve 109 is then opened to also allow purge nitrogen to flow into the flow meter 110. Metering valve 119 on flow meter is opened, and the by-pass flow rate is set to at least 1 SLPM. The purge gas then passes through flow meter outlet valve 114, through vent check valve 116 and out of the system. At this time, dry nitrogen gas is purging the panel.

The purge gas valve 103 is now closed, to stop the flow of ultra dry nitrogen into the panel. As the purge gas within the system is directed through the flow meter 110 and out the vent, the flow meter float will drop, indicating reduced flow. The steps of opening and closing the purge gas valve 103 should be repeated 3 more times (pressure cycle purging) in order to fully purge the system of entrapped air. After pressure cycle purging is complete and the flow meter 110 indicates zero flow, the flow meter inlet valve 109, the regulator isolation valve 106 and manifold station valves 105 are closed. The panel is now purged and ready for the sample gas purging Sample Purge Circuit With reference to FIG. 7, a sample gas purging process will be described. This step will remove the purge gas from the system and fill the panel with sample gas. The sample purge circuit, as previously defined, will be employed. At the start of this process all panel valves 103, 105, 106, 107, 109, 118, and 119 are closed. In addition valves 123, 130 and 132 are closed.

The three-way flow meter outlet valve 114 is configured to direct a flow to vent check valve 116 and the three-way process valve 111 is configured to receive flow from the flow meter outlet valve 114. Pressure regulator 107 is configured to deliver 0 psig (i.e. fully closed position).

Open only one manifold station valve 105 that is connected to the sample gas cylinder and open the regulator isolation valve 106. The sample gas cylinder valve 130 is quickly opened and closed to pressurize the panel system to full cylinder pressure. The pressure regulator 107 is then opened and adjusted to the desired pressure. In a preferred embodiment, the pressure regulator 107 is set to 20 psig.

The flow meter inlet valve 109 is then opened to allow sample gas to flow into the flow meter 110. Metering valve 119 on flow meter is opened, and the by-pass flow rate is set to at least 1 SLPM. The sample gas flows out of the flow meter 110, through flow meter outlet valve 114, through vent check valve 116 and is safely vented. At this time, sample gas is purging the panel.

As the sample gas within the system is directed through the flow meter 110 and out the vent, the flow meter float will drop, indicating reduced flow. The steps of opening and closing the sample gas valve 130 should be repeated 3 more times (pressure cycle purging) in order to fully purge the system of entrapped purge gas. After pressure cycle purging is complete and the flow meter 110 indicates zero flow, the flow meter inlet valve 109, the regulator isolation valve 106 and manifold station valve 105 are closed. The panel is now purged and ready for the calibration process with the sample gas.

Calibration Process

Direct Flow Circuit

With reference to FIG. 3, the process of introducing sample gas into the panel, but not through the flow meter, will be described. If multiple sample gas cylinders are to be used, it is extremely important to have only one cylinder open at a time. Otherwise cylinders could contaminate one another or they could be diluted with the other sample gas. At the start of this process all panel valves 103, 105, 106, 107, 109, and 119 are closed. In addition valves 123, 130 and 132 are closed. The flow meter outlet valve 114 is adjusted to direct a flow through the vent check valve 116 and to the system vent outlet 117. The three-way process valve 111 is configured to receive flow from the pressure regulator 107 and through the process check valve 112 and to the system outlet 113.

Next the sample cylinder valve 130 is fully opened. Open only one manifold station valve 105 that is connected to the sample gas cylinder and open the regulator isolation valve 106. The pressure regulator 107 is adjusted to the required delivery pressure setting. The system is now providing sample gas but not through the flow meter. Sample gas is directed to process valve 111, which is opened to allow gas to flow to process check valve 112. The regulator pressure and/or any relevant customer controls (not shown) are now adjusted to achieve the desired flow rate.

Flow Control Circuit

With reference to FIG. 4, the process of introducing sample gas into the panel and through the flow meter for controlled flow, with no venting of excess sample gas, will be described. The sample flow rate will be controlled by the panel to the application (analyzer) with the use of this circuit. If multiple sample gas cylinders are to be used, it is extremely important to have only one cylinder open at a time. Otherwise cylinders could contaminate one another or they could be diluted with the other sample gas. At the start of this process all panel valves 103, 105, 106, 107, 109, 119 and 130 are closed. The flow meter outlet valve 114 is adjusted to direct a flow through the three-way process valve 111. The three-way process valve 111 is configured to receive flow from the flow meter outlet valve 114.

Next the sample cylinder valve 130 is fully opened. Open only one manifold station valve 105 that is connected to the sample gas cylinder and open the regulator isolation valve 106. The pressure regulator 107 is adjusted to the required delivery pressure setting. The flow meter inlet valve 109 is opened, directing flow to the flow meter 110. The system is now ready for flow control through metering valve 119, and flow meter 110. The flow meter metering valve 119 is now adjusted to achieve the desired flow rate. The system is now providing sample gas through the flow meter. Sample gas is directed to the process valve 111, which is opened to allow gas to flow to process check valve 112 and through the system outlet 113.

Sample with Bypass Circuit

With reference to FIG. 5, the process of introducing sample gas into the panel, as well as through the flow meter, with excess sample gas being vented, will be described. If the analyzer only requires a very low calibration flow, the flow meter flow control valve 119 can be adjusted to maintain additional sample gas flow rate through the system, with the balance of the sample gas being vented 117. This reduces the sample gas retention time in the system, resulting in faster calibration (response time), and a more stable sample gas composition.

If multiple sample gas cylinders are to be used, it is extremely important to have only one cylinder open at a time. Otherwise cylinders could contaminate one another or they could be diluted with the other sample gas. At the start of this process all panel valves 103, 105, 106, 107, 109, 119 and 130 are closed. The flow meter outlet valve 114 is adjusted to direct a flow to the system vent outlet 117. The process valve 111 is adjusted to direct flow from the regulator 107 to the system outlet 113.

Next the sample gas cylinder valve 130 is fully opened. The pressure regulator 107 is adjusted to the required delivery pressure setting. The flow meter inlet valve 109 is opened. The system is now ready for sampling, with excess sample gas flowing through the flow meter 110 and then to the system vent outlet 117. The regulator pressure and flow meter metering valve are now adjusted to achieve the desired bypass flow rate while the sample gas flows to the analyzer with any relevant customer controls (not shown) now adjusted to achieve the desired flow rate.

Sample Gas Cylinder Disconnection from Panel

With reference to FIG. 7, the process of disconnecting sample gas cylinder from the panel will be described. Sample gas cylinder valve 130 is closed tightly. Process valve 111 is configured to accept a flow from the flow meter outlet valve 114, and flow meter outlet valve 114 is adjusted to direct flow to vent check valve 116. The pressure regulator 107 is set to the last pressure setting used. All other valves on the panel are closed. Manifold station valve 105 is opened. Regulator isolation valve 106 is slowly opened to allow residual pressure to pressurize pressure regulator 107. Flow meter inlet valve 109 is opened to vent residual gas from pigtails 120. With the flow meter metering valve 119 partially opened, wait for flow meter 110 to indicate zero flow. Close flow meter inlet valve 109.

With purge gas pressure regulator set to 20 psig, open purge gas valve 103, then open flow meter inlet valve 109, then close purge gas valve 103. Wait for flow meter 110 to indicate zero flow. Close flow meter inlet valve 109. The steps of opening purge gas valve 103, then opening flow meter valve 109, then closing purge gas valve 103 may need to be repeated in order to fully purge the system of sample gas. Close pressure regulator isolation valve 106. Open purge gas valve 103. Carefully disconnect sample gas cylinder 122 with purge gas flowing from the pigtail 120. Either replace with new sample cylinder or attach adapter valve 118 with valve in open position. Dead end the flow of purge gas by either tightening CGA connection nut 121 to sample cylinder valve 130 or fully closing the adapter valve 118 if used.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for utilizing a gas sampling panel, comprising:
    at least one system sample gas inlet, a purge gas inlet, a system outlet, a system vent outlet, a purge gas valve, at least one manifold station valve, a regulator isolation valve, a regulator, a flow meter inlet valve, a flow meter, a flow meter outlet valve, a relief valve, a process valve, a process check valve, a purge check valve, and a vent check valve,
    wherein
        the sample gas inlet is fluidically connected to an inlet port on at least one manifold station valve inlet,
        the purge gas inlet is fluidically connected to a purge check valve inlet port,
        a purge check valve outlet port is fluidically connected to a purge gas valve inlet port,
        a first conduit fluidically connects a purge gas valve outlet port, a manifold station valve outlet port, and a regulator isolation valve inlet port,
        a regulator isolation valve outlet port is fluidically connected to a regulator inlet port,
        the flow meter inlet valve is connected as follows:
            a second conduit fluidically connects a flow meter valve inlet port to a regulator outlet port, a first flow through gas inlet port, and a second flow through gas inlet port,
            the first flow through gas inlet port is fluidically connected to the process valve first inlet port,
            the second flow through gas inlet port is fluidically connected to a relief valve inlet port, and
            a flow meter inlet valve controlled gas outlet port is fluidically connected to a flow meter inlet port,
        a flow meter outlet port is fluidically connected to a flow meter outlet valve inlet port,
        a flow meter outlet valve first outlet port is fluidically connected to a process valve second inlet port,
        a process valve outlet port is fluidically connected to a process check valve inlet port,
        a process check valve outlet port is fluidically connected to the system outlet,
        a third conduit fluidically connects a relief valve outlet port, a flow meter outlet valve second port, and a vent check valve inlet port, and
        a vent check valve outlet port is fluidically connected to the system vent outlet,
    the method comprising:
        introducing gas into the sample gas inlet and/or the purge gas inlet, and
        removing gas from the system outlet and/or the system vent outlet.

2. The method of claim 1, comprising: configuring the gas sampling panel so that the purge gas flows both from a purge gas source through the flow meter and then to the system vent outlet, and through the process valve to the system outlet, thereby purging a gas sampling panel.

3. The method of claim 1, further comprising an adaptor valve detachably connected to a CGA connection nut, and a gas sample cylinder valve connected to a sample gas source, the method comprising: configuring the gas sampling panel so that the purge gas flows from a purge gas source through the adaptor valve, then removing the adaptor valve from the CGA connection nut, and attaching the sample gas cylinder valve to the CGA connection nut, thereby purging a gas sampling panel.

4. The method of claim 1, comprising:
    a) closing the purge gas valve, at least one manifold station valve, the regulator isolation valve, the flow meter inlet valve, the flow meter outlet valve, and the process valve;
    b) adjusting the process valve to receive a flow from the regulator,
    c) adjusting the flow meter outlet valve to direct a flow to the vent check valve,
    d) adjusting the regulator to deliver 0 psig,
    e) opening the station manifold valve,
    f) connecting a purge gas source to the purge gas inlet,
    g) opening the purge gas valve,
    h) opening the regulator isolation valve,
    i) adjusting the regulator to predetermined pressure,
    j) opening the flow meter inlet valve,
    k) opening the metering valve, and adjusting by-pass flow rate to a predetermined flow rate,
    l) closing the purge gas valve, and
    m) closing the flow meter inlet valve, the flow meter outlet valve, and the manifold station valve when the flow meter indicates 0 flow,
    thereby purging a gas sampling panel.

5. The method of claim 4, wherein the purge gas source comprises nitrogen gas with less than 20 ppb of water.

6. The method of claim 1, further comprising an adaptor valve detachably connected to a CGA connection nut, and a gas sample cylinder valve connected to a sample gas source, the method comprising:
    a) closing the purge gas valve, at least one manifold station valve, the regulator isolation valve, and the adaptor valve;
    b) opening the station manifold valve,
    c) connecting a purge gas source to the purge gas inlet,
    d) opening the purge gas valve,
    e) opening the adaptor valve, thereby allowing purge gas to flow through, f) removing the adaptor valve as purge gas flows through, and attaching the CGA connection nut to the sample gas source, and n) closing the purge gas valve, thereby purging a gas sampling panel.

7. The method of claim 1, comprising:
   a) closing the purge gas valve, at least one manifold station valve, the flow meter inlet valve, and the flow meter outlet valve;
   b) adjusting the regulator to deliver 0 psig,
   c) opening and closing a sample gas cylinder valve, thereby pressurizing the sampling panel,
   d) opening the flow meter inlet valve, thereby allowing the flow meter flow rate to drop to zero, then closing the flow meter inlet valve,
   e) adjusting the process valve to direct a flow to process check valve,
   f) opening the sample gas cylinder valve, and
   g) adjusting the regulator to the desired pressure, thereby introducing a sample gas into a sampling gas panel.

8. The method of claim 1, comprising: configuring the gas sampling panel so that the sample gas flows from the sample gas source to the system outlet, and bypasses the flow meter, thereby introducing a sample gas into a sampling gas panel.

9. The method of claim 1, comprising:
   a) closing the purge gas valve, at least one manifold station valve, the flow meter inlet valve, and the flow meter outlet valve;
   b) adjusting the regulator to deliver 0 psig,
   c) opening and closing a sample gas cylinder valve, thereby pressurizing the sampling panel,
   d) opening the flow meter inlet valve, thereby allowing the flow meter flow rate to drop to zero, then closing the flow meter inlet valve, and
   e) opening the sample gas cylinder valve,
   f) adjusting the regulator to desired pressure,
   g) adjusting flow meter outlet valve to direct a flow to process valve, and
   h) opening the flow meter inlet valve, thereby introducing a sample gas into a sampling gas panel.

10. The method of claim 1, comprising: configuring the gas sampling panel so that the sample gas flows from the sample gas source through the flow meter and then to the system outlet, thereby introducing a sample gas into a sampling gas panel.

11. The method of claim 1, comprising:
   a) closing the purge gas valve, at least one manifold station valve, the flow meter inlet valve, and the flow meter outlet valve;
   b) adjusting the regulator to deliver 0 psig,
   c) opening and closing a sample gas cylinder valve, thereby pressurizing the sampling panel,
   d) opening the flow meter inlet valve, thereby allowing the flow meter flow rate to drop to zero, then closing the flow meter inlet valve, and
   e) opening the sample gas cylinder valve,
   f) adjusting the regulator to desired pressure,
   g) adjusting process valve to direct a flow to process check valve,
   h) adjusting flow meter outlet valve to direct a flow to vent check valve,
   i) opening the flow meter inlet valve, and
   i) adjusting flow meter metering valve to desired flow rate, thereby introducing a sample gas into a sampling gas panel.

12. The method of claim 1, comprising: configuring the gas sampling panel so that the sample gas flows both from the sample gas source through the flow meter and then to the system vent outlet, and through the process valve to the system outlet, thereby introducing a sample gas into a sampling gas panel.

* * * * *